United States Patent
Shah et al.

(10) Patent No.: US 7,749,717 B2
(45) Date of Patent: Jul. 6, 2010

(54) **METHODS FOR THE DETECTION AND DIAGNOSIS OF *TRYPANOSOMA CRUZI* INFECTION**

(75) Inventors: Dinesh O. Shah, Libertyville, IL (US); Chi-Deu Chang, Green Oaks, IL (US); Gerald Schochetman, Northbrook, IL (US); Kevin Y. Cheng, Mundelein, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/583,203

(22) Filed: Oct. 19, 2006

(65) Prior Publication Data

US 2008/0096232 A1 Apr. 24, 2008

(51) Int. Cl.
G01N 33/53 (2006.01)
G01N 33/00 (2006.01)
C12Q 1/40 (2006.01)
C12Q 1/00 (2006.01)
C12M 1/34 (2006.01)
C12M 3/00 (2006.01)

(52) U.S. Cl. .............. 435/7.1; 435/4; 435/7.2; 435/7.22; 435/7.92; 435/287.2

(58) Field of Classification Search ............... None
See application file for complete search history.

(56) References Cited

U.S. PATENT DOCUMENTS

| | | | |
|---|---|---|---|
| 5,304,371 | A | 4/1994 | Reed |
| 5,413,912 | A | 5/1995 | Reed |
| 5,550,027 | A | 8/1996 | Winkler et al. |
| 5,583,204 | A | 12/1996 | Winkler et al. |
| 5,623,058 | A | 4/1997 | Winkler et al. |
| 5,645,838 | A | 7/1997 | Winkler et al. |
| 5,736,348 | A | 4/1998 | Goldenberg et al. |
| 5,756,662 | A | 5/1998 | Reed |
| 5,820,864 | A | 10/1998 | Paranhos-Baccala et al. |
| 5,876,734 | A | 3/1999 | Kirchhoff et al. |
| 5,916,572 | A | 6/1999 | Reed et al. |
| 5,942,403 | A | 8/1999 | Reed et al. |
| 6,054,135 | A | 4/2000 | Reed et al. |
| 6,203,974 | B1 | 3/2001 | Shah et al. |
| 6,228,372 | B1 | 5/2001 | Reed et al. |
| 6,228,601 | B1 | 5/2001 | Kirchhoff et al. |
| 6,270,767 | B1 | 8/2001 | Paranhos-Baccala et al. |
| 6,403,103 | B1 | 6/2002 | Paranhos-Baccala et al. |
| 6,419,933 | B1 | 7/2002 | Reed et al. |
| 6,458,922 | B1 | 10/2002 | Zrein |
| 6,682,900 | B1 | 1/2004 | Travassos et al. |
| 6,933,110 | B1 | 8/2005 | Paranhos-Baccala et al. |
| 2003/0099929 | A1 | 5/2003 | Vojdani |
| 2004/0132077 | A1 | 7/2004 | Kirchhoff et al. |
| 2005/0277113 | A1 | 12/2005 | Vojdani |

FOREIGN PATENT DOCUMENTS

| | | |
|---|---|---|
| EP | 0 138 101 A1 | 4/1985 |
| EP | 0 397 129 B1 * | 7/1996 |
| EP | 0 649 536 B1 | 4/2002 |
| WO | 91/15584 | 10/1991 |
| WO | 97/05468 | 2/1997 |
| WO | 99/05528 | 2/1999 |
| WO | WO 2004/050852 A2 * | 6/2004 |

OTHER PUBLICATIONS

Chang et al. Transfusion vol. 46 issue 10 p. 1737-1744, Oct. 2006 published online Aug. 23, 2006.*
da Silveira et al. Trends in Parasitology vol. 17, p. 286-291 Jun. 2001.*
Umezawa et al, Journal of Clinical Microbiology, Sep. 1996, p. 2143-2147 and Fabrizi et al. Am J Nephrol 2001; 21:104-111.*
Fabrizi et al. Am J Nephrol 2001; 21:104-111.*
Shah et al. Transfusion, Sep. 2006 vol. 46, abstract supplement.*
Aguirre et al. J. clin. Microbiology, 44 (10):3768-3774 Oct. 1, 2006.*
Abbas et al. Cellular and Molecular Immunology 4th edition, 2000, p. 11.*
Tyler et al Int. Journal for Parasitology 31 (2001) 472-481.*
de Oliveira Santos Braz J Infect Dis vol. 6 (2002): 317-321.*
Pinho et al Act Tropica 72 (1999): 31-38.*
Parija et al Parasitology Today 14 (1998): 5-6.*
Abate, et al., Biol. Res., 26, 121-130 (1993).
Aguero-Rosenfeld, et al., Clinical Microbiology Reviews, 18(3), 484-509, (2005).
Aguirre, et al., Journal of Clinical Microbiology, 44(10), 3768-3774 (2006).
Almeida, et al., Transfusion, 37, 850-857 (1997).
Berrizbeitia, et al., Journal of Clinical Microbiology, 44(2), 291-296 (2006).
Cetron, et al., Acta Tropica, 50, 259-266 (1992).
Chang, et al., Transfusion, 46, 1737-1744 (2006).
Cotrim, et al., Journal of Clinical Microbiology, 28(3), 519-524 (1990).
da Silveira, E.S. Umezawa, and A.O. Luquetti, 17(6), 286-291 (2001).
Frasch, et al., Parasitology Today, 7(6), 148-151 (1991).
Gomes, et al., Am. J. Trop. Med. Hyg. 60(2), 205-210 (1999).
Kirchhoff, et al., American trypanosomiasis. *In* Guerrant, et al., editors, Tropical Infectious Diseases: Principles, Pathogens & Practice, p. 1082-1094, Churchill Livingstone, New York, (2006).
Gruber and Zingal, Experimental Parasitology, 76, 1-12, (1993).
Houghton, et al., Journal of Infectious Diseases, 179, 1226-1234 (1999).
Jazin, et al., Parasitology, 110, 61-69 (1995).
Kirchhoff, et al., Transfusion, 46, 298-304, (2006).

(Continued)

*Primary Examiner*—Robert Mondesi
*Assistant Examiner*—Oluwatosin Ogunbiyi
(74) *Attorney, Agent, or Firm*—Cheryl L. Becker; Audrey L. Bartnicki

(57) ABSTRACT

The present invention relates to the diagnosis of *Trypanosoma cruzi* infection.

8 Claims, 2 Drawing Sheets

OTHER PUBLICATIONS

Kirchhoff, et al., Journal of Infectious Diseases, 155(3), 561-564 (1987).
Krautz, et al., Am. J. Trop. Med. Hyg., 58(2), 137-143 (1998).
Lafaille, et al., Molecular and Biochemical Parasitology, 35(2), 127-136 (1989).
Leiby, et al., Journal of Clinical Microbiology, 38(2), 639-642 (2000).
Leiby, et al., New England Journal of Medicine, 341(16), 1237-1239(1999).
Leiby, et al., Transfusion, 42, 549-555 (2002).
Lesenechal, et al., Molecular and Biochemical Parasitology, 87, 193-204 (1997).
Luquetti, et al., Diagnostic Microbiology and Infectious Disease, 46, 265-271 (2003).
Maldarelli, et al., Diagnosis of human immunodeficiency virus infection. In Mandell, Douglas, and Bennett's, Principles and Practice of Infectious Diseases, John Wiley & Sons, New York, 1, 1506-1527 (2005).
Mendes, et al., Journal of Clinical Microbiology, 35(7), 1829-1834 (1997).
Norris, et al., Infection and Immunity, 65(2), 349-357 (1997).
Oelemann, et al., Transfusion, 39, 177-717(1999).
Ponce, et al., Journal of Clinical Microbiology, 43(10), 5065-5068 (2005).
Saez-Alquez, et al., Journal of Clinical Microbiology, 38(2), 581-854 (2000).
Schmunis, et al., Clinical Microbiology Reviews, 18(1), 12-29 (2005).
Shah, et al., Transfusion, 46 Supplement:111A (2006).
Silveira-Lacerda, et al., Vox Sanguinis, 87, 204-207 (2004).
Telles, et al., FEMS Immunology and Medical Microbiology, 24, 123-130 (1999).
Tobler, et al., Transfusion, 40, 917-923 (2000).
Umezawa, et al., Journal of Clinical Microbiology, 34(9), 2143-2147 (1996).
Umezawa, et al., Journal of Clinical Microbiology, 37(5), 1554-1560 (1999).
World Health Organization Geneva, Control of Chagas Disease (2000).
Innogenetics, INNO-LIA Chagas AB Research Version, Product Insert Sheet (undated).
Cheng, K.Y., et al. "Immunoblot Assay Using Recombinant Antigens as a Supplemental Test to Confirm the Presence of Antibodies to *Trypanosoma cruzi*", Clin. & Vacc. Immunol., vol. 14, No. 4, pp. 355-361 (2007).
Ferreira, A.W., et al., "Enzyme-Linked Immunosorbent Assay for Serological Diagnosis of Chagas' Disease Employing a *Trypanosoma cruzi* Recombinant Antigen That Consists of Four Different Peptides", J. of Clin. Microbiol., vol. 39, No. 12, pp. 4390-4395 (2001).
Saez-Alquezar, A., et al. "Serological Confirmation of Chagas" Disease by a Recombinant and Peptide Antigen Line immunoassay: INNO-LIA Chagas, Journ of Cklin Microb, vol. 38(2) pp. 851-854 (2000).
Sackett, et al. "A Basic Science for Clinical Medicine": Clinical Epidemiology, p. 106-107 (1985)—First Edition.
Sackett, et al. "A Basic Science for Clinical Medicine": Clinical Epidemiology, p. 100-110 (1985) Second Edition.
Zayas, et al., MMWP, 51(10), 210-212 (2001).
Mascola, et al., MMWR, 55(29), 798-800 (2006).

* cited by examiner

SEQUENCE LISTING

```
<160> NUMBER OF SEQ ID NOS: 8

<210> SEQ ID NO 1
<211> LENGTH: 693
<212> TYPE: PRT
<213> ORGANISM: T. cruzi

<400> SEQUENCE: 1

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
```

```
              65                  70                  75                  80
Leu Phe Lys Asn Gly Glu Val Ala Ala Thr Lys Val Gly Ala Leu Ser
                 85                  90                  95
Lys Gly Gln Leu Lys Glu Phe Leu Asp Ala Asn Leu Ala Gly Ser Gly
                100                 105                 110
Ser Gly His Met His His His His His His Ser Ser Gly Leu Val Pro
                115                 120                 125
Arg Gly Ser Gly Met Lys Glu Thr Ala Ala Ala Lys Phe Glu Arg Gln
        130                 135                 140
His Met Asp Ser Pro Asp Leu Gly Thr Asp Asp Asp Lys Ala Met
145                 150                 155                 160
Ala Gln Leu Gln Gln Ala Glu Asn Asn Ile Thr Asn Ser Lys Lys Glu
                165                 170                 175
Met Thr Lys Leu Arg Glu Lys Val Lys Lys Ala Glu Lys Glu Lys Leu
                180                 185                 190
Asp Ala Ile Asn Arg Ala Thr Lys Leu Glu Glu Glu Arg Asn Gln Ala
                195                 200                 205
Tyr Lys Ala Ala His Lys Ala Glu Glu Lys Ala Lys Thr Phe Gln
        210                 215                 220
Arg Leu Ile Thr Phe Glu Ser Glu Asn Ile Asn Leu Lys Lys Arg Pro
225                 230                 235                 240
Asn Asp Ala Val Ser Asn Arg Asp Lys Lys Asn Ser Glu Thr Ala
                245                 250                 255
Lys Thr Asp Glu Val Glu Lys Gln Arg Ala Ala Glu Ala Ala Lys Ala
                260                 265                 270
Val Glu Thr Glu Lys Gln Arg Ala Ala Glu Ala Thr Lys Val Ala Glu
                275                 280                 285
Ala Glu Lys Arg Lys Ala Ala Glu Ala Ala Lys Ala Val Glu Thr Glu
                290                 295                 300
Lys Gln Arg Ala Ala Glu Ala Thr Lys Val Ala Glu Ala Glu Lys Gln
305                 310                 315                 320
Lys Ala Ala Glu Ala Ala Lys Ala Val Glu Thr Glu Lys Gln Arg Ala
                325                 330                 335
Ala Glu Ala Thr Lys Val Ala Glu Ala Glu Lys Gln Arg Ala Ala Glu
                340                 345                 350
Ala Met Lys Val Ala Glu Ala Glu Lys Gln Lys Ala Ala Glu Ala Ala
                355                 360                 365
Lys Ala Val Glu Thr Glu Lys Gln Arg Ala Ala Glu Ala Thr Lys Val
        370                 375                 380
Ala Glu Ala Glu Lys Gln Lys Ala Ala Glu Ala Ala Lys Ala Val Glu
385                 390                 395                 400
Thr Glu Lys Gln Arg Ala Ala Glu Ala Thr Lys Val Ala Glu Ala Glu
                405                 410                 415
Lys Gln Lys Ala Ala Glu Ala Ala Lys Ala Val Glu Thr Glu Lys Gln
                420                 425                 430
Arg Ala Ala Glu Ala Thr Lys Val Ala Glu Ala Glu Lys Asp Ile Asp
        435                 440                 445
Pro Met Gly Ala Cys Gly Ser Lys Asp Ser Thr Ser Asp Lys Gly Leu
        450                 455                 460
Ala Ser Asp Lys Asp Gly Lys Asn Ala Lys Asp Arg Lys Glu Ala Trp
465                 470                 475                 480
Glu Arg Ile Arg Gln Ala Ile Pro Arg Glu Lys Thr Ala Glu Ala Lys
                485                 490                 495
```

-continued

```
Gln Arg Arg Ile Glu Leu Phe Lys Lys Phe Asp Lys Asn Glu Thr Gly
            500                 505                 510

Lys Leu Cys Tyr Asp Glu Val His Ser Gly Cys Leu Glu Val Leu Lys
        515                 520                 525

Leu Asp Glu Phe Thr Pro Arg Val Arg Asp Ile Thr Lys Arg Ala Phe
    530                 535                 540

Asp Lys Ala Arg Ala Leu Gly Ser Lys Leu Glu Asn Lys Gly Ser Glu
545                 550                 555                 560

Asp Phe Val Glu Phe Leu Glu Phe Arg Leu Met Leu Cys Tyr Ile Tyr
                565                 570                 575

Asp Phe Phe Glu Leu Thr Val Met Phe Asp Glu Ile Asp Ala Ser Gly
            580                 585                 590

Asn Met Leu Val Asp Glu Glu Phe Lys Arg Ala Val Pro Arg Leu
        595                 600                 605

Glu Ala Trp Gly Ala Lys Val Glu Asp Pro Ala Leu Phe Lys Glu
    610                 615                 620

Leu Asp Lys Asn Gly Thr Gly Ser Val Thr Phe Asp Glu Phe Ala Ala
625                 630                 635                 640

Trp Ala Ser Ala Val Lys Leu Asp Ala Asp Gly Asp Pro Asp Asn Val
                645                 650                 655

Pro Glu Ser Pro Arg Pro Met Gly Ile Asp Ile Gly Ser Glu Phe Glu
            660                 665                 670

Leu Arg Arg Gln Ala Cys Gly Arg Thr Arg Ala Pro Pro Pro Pro
    675                 680                 685

Leu Arg Ser Gly Cys
    690

<210> SEQ ID NO 2
<211> LENGTH: 994
<212> TYPE: PRT
<213> ORGANISM: T. cruzi

<400> SEQUENCE: 2

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Lys Ala Met
145                 150                 155                 160

Gly Tyr Leu Trp Ile Arg Ile Arg Ser Ala Arg Gln Ala Ser Thr Asp
```

-continued

```
            165                 170                 175
Lys Leu Lys Leu Asn Gln Gln Asn Lys Pro His Ile Ala Asn Asn Lys
            180                 185                 190
Gln Lys Thr Thr Leu Glu Lys Thr Gln Thr Glu Gln Lys Thr Ala Pro
            195                 200                 205
Phe Gly Gln Ala Ala Ala Gly Asp Lys Pro Ser Pro Phe Gly Gln Ala
            210                 215                 220
Ala Ala Gly Asp Lys Pro Ser Pro Phe Gly Gln Ala Ala Ala Gly Gly
225                 230                 235                 240
Lys Pro Pro Phe Gly Gln Ala Ala Ala Gly Asp Lys Pro Ser Pro
            245                 250                 255
Phe Gly Gln Ala Ala Ala Gly Asp Lys Pro Pro Phe Gly Gln Ala
            260                 265                 270
Ala Ala Gly Asp Lys Pro Ser Pro Phe Gly Gln Ala Ala Ala Gly Asp
            275                 280                 285
Lys Pro Pro Phe Gly Gln Ala Ala Ala Gly Asp Lys Pro Pro
            290                 295                 300
Phe Gly Gln Ala Ala Ala Gly Asp Lys Pro Pro Phe Gly Gln Ala
305                 310                 315                 320
Ala Ala Gly Asp Lys Pro Pro Phe Gly Gln Ala Ala Ala Gly Asp
            325                 330                 335
Lys Pro Ser Leu Phe Gly Gln Ala Ala Ala Gly Asp Lys Pro Ser Pro
            340                 345                 350
Phe Gly Gln Gly Thr Ala Phe Asp Ala Ser Arg Ser Thr Val Phe Ala
            355                 360                 365
Asn Ala Pro Gly Val Ala Leu Asp Lys Asp Pro Arg Arg Asn Ala Lys
            370                 375                 380
Glu Ile Ala Ala Leu Glu Glu Ser Met Asn Ala Arg Ala Gln Glu Leu
385                 390                 395                 400
Ala Arg Glu Lys Lys Leu Ala Asp Arg Ala Phe Leu Asp Gln Lys Pro
            405                 410                 415
Glu Gly Val Pro Leu Arg Glu Leu Pro Leu Asp Asp Asp Ser Asp Phe
            420                 425                 430
Val Ala Met Glu Gln Glu Arg Arg Gln Leu Leu Asp Lys Asp Pro Arg
            435                 440                 445
Arg Asn Ala Lys Glu Ile Ala Ala Leu Glu Glu Ser Met Asn Ala Arg
            450                 455                 460
Ala Gln Glu Leu Ala Arg Glu Lys Lys Leu Ala Asp Arg Ala Phe Leu
465                 470                 475                 480
Asp Gln Lys Pro Glu Gly Val Pro Leu Arg Glu Leu Pro Leu Asp Asp
            485                 490                 495
Asp Ser Asp Phe Val Ala Met Glu Gln Glu Arg Arg Gln Leu Leu Asp
            500                 505                 510
Lys Asp Pro Arg Arg Asn Ala Lys Glu Ile Ala Ala Leu Glu Glu Ser
            515                 520                 525
Met Asn Ala Arg Ala Gln Glu Leu Ala Arg Glu Lys Lys Leu Ala Asp
            530                 535                 540
Arg Ala Phe Leu Asp Gln Lys Pro Glu Gly Val Pro Leu Arg Glu Leu
545                 550                 555                 560
Pro Leu Asp Asp Asp Ser Asp Phe Val Ala Met Glu Gln Glu Arg Arg
            565                 570                 575
Gln Leu Leu Asp Lys Asp Pro Arg Arg Asn Ala Lys Glu Ile Ala Ala
            580                 585                 590
```

```
Leu Glu Glu Ser Met Asn Ala Arg Ala Gln Glu Leu Ala Arg Glu Lys
            595                 600                 605

Lys Leu Ala Asp Arg Ala Phe Leu Asp Gln Lys Pro Glu Gly Val Pro
    610                 615                 620

Leu Arg Glu Leu Pro Leu Asp Asp Ser Asp Phe Val Ala Met Glu
625                 630                 635                 640

Gln Glu Arg Arg Gln Leu Leu Asp Lys Asp Pro Arg Arg Asn Ala Lys
                645                 650                 655

Glu Ile Ala Ala Leu Glu Glu Ser Met Asn Ala Arg Ala Gln Glu Leu
            660                 665                 670

Ala Arg Glu Lys Lys Leu Ala Asp Arg Ala Phe Leu Asp Gln Lys Pro
        675                 680                 685

Glu Gly Val Pro Leu Arg Glu Leu Pro Leu Asp Asp Asp Ser Asp Phe
    690                 695                 700

Val Ala Met Glu Gln Glu Arg Arg Gln Leu Leu Asp Lys Asp Pro Arg
705                 710                 715                 720

Arg Asn Ala Lys Glu Ile Ala Ala Leu Glu Glu Ser Met Asn Ala Arg
                725                 730                 735

Ala Gln Glu Leu Ala Arg Glu Lys Lys Leu Ala Asp Arg Ala Phe Leu
            740                 745                 750

Asp Gln Lys Pro Glu Gly Val Pro Leu Arg Glu Leu Pro Leu Asp Asp
        755                 760                 765

Asp Ser Asp Phe Val Ala Met Glu Gln Glu Arg Arg Gln Leu Leu Asp
    770                 775                 780

Lys Asp Pro Arg Arg Asn Ala Lys Glu Ile Ala Ala Leu Glu Glu Ser
785                 790                 795                 800

Met Asn Ala Arg Ala Gln Glu Leu Ala Arg Glu Lys Lys Leu Ala Asp
                805                 810                 815

Arg Ala Phe Leu Asp Gln Lys Pro Glu Gly Val Pro Leu Arg Glu Leu
            820                 825                 830

Pro Leu Asp Asp Asp Ser Asp Phe Val Ala Met Glu Gln Glu Arg Arg
        835                 840                 845

Gln Leu Leu Asp Lys Asp Pro Arg Arg Asn Ala Lys Glu Ile Ala Ala
    850                 855                 860

Leu Glu Glu Ser Met Asn Ala Arg Ala Gln Glu Leu Ala Arg Glu Lys
865                 870                 875                 880

Lys Leu Ala Asp Arg Ala Phe Leu Asp Gln Lys Pro Glu Gly Val Pro
                885                 890                 895

Leu Arg Glu Leu Pro Leu Asp Asp Asp Ser Asp Phe Val Ala Met Glu
            900                 905                 910

Gln Glu Arg Arg Gln Leu Leu Asp Lys Asp Pro Arg Arg Asn Ala Lys
        915                 920                 925

Glu Ile Ala Ala Leu Glu Glu Ser Met Asn Ala Arg Ala Gln Glu Leu
    930                 935                 940

Ala Arg Glu Lys Lys Leu Ala Asp Arg Ala Phe Leu Asp Gln Lys Pro
945                 950                 955                 960

Glu Gly Val Pro Leu Arg Glu Leu Pro Leu Asp Asp Asp Ser Asp Phe
                965                 970                 975

Val Ala Met Glu Gln Glu Arg Arg Gln Leu Leu Glu His His His His
            980                 985                 990

His His
```

<210> SEQ ID NO 3
<211> LENGTH: 722
<212> TYPE: PRT
<213> ORGANISM: T. cruzi

<400> SEQUENCE: 3

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Lys Ala Met
145                 150                 155                 160

Gly Tyr Leu Trp Ile Arg Ile Arg Pro Ser Gly Ala Asp Pro Thr Tyr
                165                 170                 175

Arg Phe Ala Asn His Ala Phe Thr Leu Val Ala Ser Val Thr Ile His
            180                 185                 190

Glu Val Pro Ser Val Ala Ser Pro Leu Leu Gly Ala Ser Leu Asp Ser
        195                 200                 205

Ser Gly Gly Lys Lys Leu Leu Gly Leu Ser Tyr Asp Glu Lys His Gln
    210                 215                 220

Trp Gln Pro Ile Tyr Gly Ser Thr Pro Val Thr Pro Thr Gly Ser Trp
225                 230                 235                 240

Glu Met Gly Lys Arg Tyr His Val Val Leu Thr Met Ala Asn Lys Ile
                245                 250                 255

Gly Ser Val Tyr Ile Asp Gly Glu Pro Leu Glu Gly Ser Gly Gln Thr
            260                 265                 270

Val Val Pro Asp Glu Arg Thr Pro Asp Ile Ser His Phe Tyr Val Gly
        275                 280                 285

Gly Tyr Gly Arg Ser Asp Met Pro Thr Ile Ser His Val Thr Val Asn
    290                 295                 300

Asn Val Leu Leu Tyr Asn Arg Gln Leu Asn Ala Glu Glu Ile Arg Thr
305                 310                 315                 320

Leu Phe Leu Ser Gln Asp Leu Ile Gly Thr Glu Ala His Met Gly Ser
                325                 330                 335

Ser Ser Gly Ser Ser Ala His Gly Thr Pro Ser Ile Pro Val Asp Ser
            340                 345                 350

Ser Ala His Gly Thr Pro Ser Thr Pro Val Asp Ser Ser Ala His Gly
        355                 360                 365

Thr Pro Ser Thr Pro Val Asp Ser Ser Ala His Gly Thr Pro Ser Thr
    370                 375                 380
```

```
Pro Val Asp Ser Ser Ala His Gly Thr Pro Ser Thr Pro Val Asp Ser
385                 390                 395                 400

Ser Ala His Gly Lys Pro Ser Thr Pro Ala Asp Ser Ser Ala His Ser
            405                 410                 415

Thr Pro Ser Thr Pro Ala Asp Ser Ser Ala His Ser Thr Pro Ser Ile
        420                 425                 430

Pro Ala Asp Ser Ser Ala His Ser Thr Pro Ser Ala Pro Ala Asp Asn
            435                 440                 445

Gly Ala Asn Gly Thr Val Leu Ile Leu Ser Thr His Asp Ala Tyr Arg
        450                 455                 460

Pro Val Asp Pro Ser Ala Tyr Lys Arg Ala Leu Pro Gln Glu Glu Gln
465                 470                 475                 480

Glu Asp Val Gly Pro Arg His Val Asp Pro Asp His Phe Arg Ser Thr
                485                 490                 495

Ser Thr Thr His Asp Ala Tyr Arg Pro Val Asp Pro Ser Ala Tyr Lys
            500                 505                 510

Arg Ala Leu Pro Gln Glu Glu Gln Glu Asp Val Gly Pro Arg His Val
            515                 520                 525

Asp Pro Asp His Phe Arg Ser Thr Ser Thr Thr His Asp Ala Tyr Arg
530                 535                 540

Pro Val Asp Pro Ser Ala Tyr Lys Arg Ala Leu Pro Gln Glu Glu Gln
545                 550                 555                 560

Glu Asp Val Gly Pro Arg His Val Asp Pro Asp His Phe Arg Ser Thr
                565                 570                 575

Ser Thr Thr His Asp Ala Tyr Arg Pro Val Asp Pro Ser Ala Tyr Lys
            580                 585                 590

Arg Ala Leu Pro Gln Glu Glu Gln Glu Asp Val Gly Pro Arg His Val
            595                 600                 605

Asp Pro Asp His Phe Arg Ser Thr Thr His Asp Ala Tyr Arg Pro Val
610                 615                 620

Asp Pro Ser Ala Tyr Lys Arg Ala Leu Pro Gln Glu Glu Gln Glu Asp
625                 630                 635                 640

Val Gly Pro Arg His Val Asp Pro Asp His Phe Arg Ser Thr Thr His
                645                 650                 655

Asp Ala Tyr Arg Pro Val Asp Pro Ser Ala Tyr Lys Arg Ala Leu Pro
            660                 665                 670

Gln Glu Glu Gln Glu Asp Val Gly Pro Arg His Val Asp Pro Asp His
            675                 680                 685

Phe Arg Ser Thr Ser Ser Thr Thr Thr Thr Thr Glu Ile Arg Leu
690                 695                 700

Leu Thr Lys Pro Glu Arg Lys Leu Ser Trp Leu Leu Pro Pro Leu Ser
705                 710                 715                 720

Asn Asn

<210> SEQ ID NO 4
<211> LENGTH: 85
<212> TYPE: PRT
<213> ORGANISM: T. cruzi

<400> SEQUENCE: 4

Met Gly His His His His His His Gly Asp Lys Pro Ser Pro Phe Gln
1               5                   10                  15

Ala Ala Ala Gly Asp Lys Pro Ser Pro Phe Gly Gln Ala Ala Glu Pro
            20                  25                  30
```

-continued

```
Lys Ser Ala Glu Pro Lys Pro Ala Glu Pro Lys Ser Lys Ala Ala Ile
        35                  40                  45

Ala Pro Ala Lys Ala Ala Ala Ala Pro Ala Lys Ala Ala Thr Ala Pro
        50                  55                  60

Ala Ser Ser Met Pro Ser Gly Thr Ser Glu Glu Gly Ser Arg Gly Gly
65                  70                  75                  80

Ser Ser Met Pro Ala
            85

<210> SEQ ID NO 5
<211> LENGTH: 21
<212> TYPE: PRT
<213> ORGANISM: T. cruzi

<400> SEQUENCE: 5

Gly Asp Lys Pro Ser Pro Phe Gln Ala Ala Ala Gly Asp Lys Pro Ser
1               5                   10                  15

Pro Phe Gly Gln Ala
            20

<210> SEQ ID NO 6
<211> LENGTH: 15
<212> TYPE: PRT
<213> ORGANISM: T. cruzi

<400> SEQUENCE: 6

Ala Glu Pro Lys Ser Ala Glu Pro Lys Pro Ala Glu Pro Lys Ser
1               5                   10                  15

<210> SEQ ID NO 7
<211> LENGTH: 21
<212> TYPE: PRT
<213> ORGANISM: T. cruzi

<400> SEQUENCE: 7

Lys Ala Ala Ile Ala Pro Ala Lys Ala Ala Ala Ala Pro Ala Lys Ala
1               5                   10                  15

Ala Thr Ala Pro Ala
            20

<210> SEQ ID NO 8
<211> LENGTH: 20
<212> TYPE: PRT
<213> ORGANISM: T. cruzi

<400> SEQUENCE: 8

Ser Ser Met Pro Ser Gly Thr Ser Glu Glu Gly Ser Arg Gly Gly Ser
1               5                   10                  15

Ser Met Pro Ala
            20
```

METHODS FOR THE DETECTION AND DIAGNOSIS OF *TRYPANOSOMA CRUZI* INFECTION

RELATED APPLICATION INFORMATION

None.

FIELD OF THE INVENTION

The present invention relates to the diagnosis of *Trypanosoma cruzi* infection. More specifically, the present invention relates to methods of identifying and diagnosing *Trypanosoma cruzi* infection using a novel combination of four recombinant polypeptides.

BACKGROUND OF THE PRESENT INVENTION

*Trypanosoma cruzi* ("*T. cruzi*"), the protozoan parasite that causes Chagas' disease, or American trypanosomiasis, is endemic in Central and South America as well as in Mexico. Most infected persons, after a mild acute phase, enter the life-long indeterminate phase that is characterized by a lack of symptoms, low parasitemias, and antibodies to a variety of *T. cruzi* antigens. Approximately 10-30% of persons with chronic *T. cruzi* infections, however, develop cardiac or gastrointestinal dysfunction as a consequence of the persistent presence of the parasite. Chemotherapy is largely ineffective, particularly for chronic infections. Roughly 25,000 of the estimated 12 million people in the endemic countries who are chronically infected with *T. cruzi* die of the illness each year, typically due to cardiac rhythm disturbances or congestive heart failure (See, Kirchoff, L. V., "American trypanosomiasis (Chagas' disease) in Tropical Infectious Diseases: Principles, Pathogens and Practice, R. L. Guerrant et al., editors, p. 1082-1094, Churchill Livingstone, N.Y. 2006).

In endemic areas *T. cruzi* is transmitted mainly by blood-sucking triatomine insects. Transmission can also occur by transfusion of blood donated by chronically infected persons, and historically this route of transmission was important in the endemic countries prior to the implementation of blood screening programs (See, Schunis, G. A., *Clin. Microbiol. Rev.*, 18:12-29 (2000)). There is no vaccine for preventing transmission of *T. cruzi*. During the last few decades emigration from Chagas-endemic countries to the U.S. has increased markedly. Approximately 13 million such immigrants now live in the U.S., and an estimated 80,000-120,000 of these persons are infected with *T. cruzi* (See, Kirchoff, L. V., et al., *Transfusion*, 46:298-304 (2006)). Their presence creates a risk of transfusion-related transmission of the parasite in the U.S. Five instances of transfusion-related Chagas disease have already been reported in the U.S., and blood bank authorities agree that a much larger number of undiagnosed cases have likely occurred (See, Leiby, D. A., et al., *N. Engl. J. Med.*, 341:1237-1239 (1999) and Young, C. T., "Transfusion acquired *Trypanosoma cruzi* infection," *Transfusion*, In press (2007)). Currently the U.S. blood supply is not screened for *T. cruzi*, as no blood screening assay has been cleared by the FDA. Hence, *T. cruzi* infection is a threat to the U.S. blood supply. *T. cruzi* can also be transmitted by transplantation of organs obtained from chronically infected persons. Numerous reports of such transmission have been reported in the endemic countries, and it is unclear how many have gone undetected in the U.S. (See, Mascola, L., et al., *MMWR*, 55:798-780 (2006) and Zayas, C. F., et al., *MMWP*, 51:210-212 (2001)).

Laboratory diagnosis of chronic *T. cruzi* infection is complex. Demonstration of the parasite by hemoculture or xenodiagnosis is time-consuming, insensitive, and expensive. In contrast, serologic assays for antibodies to *T. cruzi* are well suited for rapid and inexpensive diagnosis of the infection. Conventional tests, such as indirect hemagglutination assay ("IHA"), indirect immunofluorescence assay ("IFA"), and enzyme-linked immunosorbent assay ("ELISA"), are used widely in the endemic countries. Most are based on whole or semi-purified antigenic fractions from *T. cruzi* epimastigotes grown in axenic culture. A persistent problem with the conventional assays has been the occurrence of inconclusive and false-positive results (Almeida, I. C., et al., *Transfusion*, 37:850-857 (1997), Kirchoff, L. V., et al., *Transfusion*, 46:298-304 (2006) and Leiby, D. A., et al., *J. Clin. Microbiol.*, 38:639-642 (2000)). There is no consensus on which parasite antigen preparation is best for detecting antibodies to *T. cruzi*. The Pan American Health Organization and other expert groups have recommended that donated blood be tested by at least two different methods run in parallel (See, "Control of Chagas Disease", World Health Organization, Geneva (2000)). This approach carries with it an enormous logistical and economic burden for blood banks.

Thus, there is a need in the art for a supplemental assay for use in clinical laboratories and blood banks. No assay has been uniformly accepted as the gold standard for the serologic diagnosis of *T. cruzi* infection. PCR-based assays lack the sensitivity necessary for this role (See, Gomes, M. L., *Am. J. Trop. Med. Hyg.*, 60:205-210 (1999)). A radioimmune precipitation assay ("RIPA"), which is a highly sensitive and specific test with easily interpreted results was developed nearly two decades ago and has been suggested for use as a confirmatory test in the U.S. (See, Kirchoff, L. V., et al., *J. Infect. Dis.*, 155:561-564 (1987)). Although the RIPA has been used as a confirmatory assay in more than 20 research projects reported to date (See, Kirchoff, L. V., et al., *Transfusion*, 46:298-304 (2006) and Leiby, D. A., et al., *Transfusion*, 42:549-555 (2002)), its sensitivity and specificity have not been systematically validated. Moreover, the complexity of the RIPA would make its widespread use outside of research settings difficult (See, Leiby, D. A., et al., *J. Clin. Microbiol.*, 38:639-642 (2000)).

Immunoblot assays have also been studied as supplemental tests for antibodies to *T. cruzi*. Some years ago an immunoblot assay based on a *T. cruzi* protein antigen fraction from epimastigotes bound to a nitrocellulose membrane was proposed as a supplemental test for Chagas' disease (See, Mendes, R. P., et al., *J. Clin. Microbiol.*, 35:1829-1834 (1997)). A similar role has been proposed for an immunoblot assay based on a trypomastigote excreted-secreted antigen fraction ("TESA") produced in cultures of *T. cruzi*-infected mammalian cells (See, Berrizbeitia, M., et al., *J. Clin. Microbiol.*, 44:291-296 (2006), Umezawa, E. S., *J. Clin. Microbiol.*, 34:2143-2147 (1996)). The biohazard inherent in manipulating cultures of live parasites and the difficulty of producing these complex antigen mixtures with lot-to-lot consistency are major disadvantages of assays based on antigens from culture such as these two. Additionally, none of these tests have been adopted as a confirmatory test and none has been developed commercially. Another assay, namely, the INNO-LIA Chagas assay, contains seven *T. cruzi* single-domain test bands on a plastic strip. However, the fact that seven distinct recombinant antigens are present on the strip could be a limiting factor in terms of its sensitivity. Moreover, having seven test bands complicates the interpretation protocol.

Thereupon, there remains a need in the art for an assay for *T. cruzi* that shows a high level of sensitivity and specification,

SUMMARY OF THE INVENTION

In one embodiment, the present invention relates to a method of identifying *Trypanosoma cruzi* in a test sample. The method comprises the steps of:

contacting a test sample from a human with the four recombinant polypeptides FP3, FP6, FP10 and TcF; and detecting the binding of antibodies present in said test sample to at least two of said recombinant polypeptides, the presence of said binding of said antibodies to at least two of said recombinant polypeptides indicating the presence of *Trypanosoma cruzi* in said test sample.

The test sample contacted in the above method can be blood, serum, plasma, saliva, cerebrospinal fluid, urine or other appropriate sample. Additionally, the above method can further comprise the step of contacting the test sample with at least one additional recombinant polypeptide selected from the group consisting of JL8, TCR27, JL7, TCR39, PEP-2, Ag36, JL9, TCNA, TcLo1.2, TS, TcD, TcE, FCaBP, Tc-28, Tc-40, FL-160, CEA, CRP, TcP2$\beta_N$-C29 and SA85-1.1.

In another embodiment, the present invention relates to a solid phase having immobilized thereon four recombinant polypeptides FP3, FP6, FP10 and TcF, and a first control and a second control, wherein either the first control or the second control is immobilized on the solid phase in a concentration that is less than the other control.

The polypeptides can be arranged on the solid phase as separate bands (or, e.g., as spots or dots). The solid phase can be selected from the group consisting of nitrocellulose, nylon, plastic and paper, or other appropriate solid phase. Additionally, the solid phase can be a strip having said polypeptides immobilized thereon. The solid phase can have further immobilized thereon at least one additional recombinant polypeptide selected from the group consisting of JL8, TCR27, JL7, TCR39, PEP-2, Ag36, JL9, TCNA, TcLo1.2, TS, TcD, TcE, FCaBP, Tc-28, Tc-40, FL-160, CEA, CRP, TcP2$\beta_N$-C29 and SA85-1.1.

In yet another embodiment, the present invention relates to a method of diagnosing *Trypanosoma cruzi* in a subject. The method comprising the steps of:

contacting a test sample obtained from a subject with a solid phase, wherein said solid phase has immobilized thereon the four recombinant polypeptides FP3, FP6, FP10 and TcF as separate test bands, and a first control and a second control, wherein either the first control or the second control is immobilized on the solid phase in a concentration that is less than the other control so as to comprise a low control;

contacting the solid phase with at least one detection reagent;

detecting the binding of antibodies present in the test sample by identifying the presence of a signal at each of the test bands;

comparing the intensity of any signal identified at a test band for a recombinant polypeptide with the intensity of the signal of the low control;

wherein the identification of a signal at least two test bands of the recombinant polypeptides indicates the presence of *T. cruzi* in said test sample, provided that at least one of the signals identified at a test band for a recombinant polypeptide has an intensity comparable to that of the low control.

The test sample contacted in the above method can be blood, serum, plasma, saliva, cerebrospinal fluid, urine or other appropriate sample. The polypeptides immobilized in the solid phase used in the above method can be arranged on the solid phase as separate bands (or, e.g., as spots or dots). Moreover, the solid phase can be selected from the group consisting of nitrocellulose, nylon, plastic and paper, or other appropriate solid phase. Additionally, the solid phase can be a strip having said polypeptides immobilized thereon. The solid phase can further have immobilized thereon at least one additional recombinant polypeptide selected from the group consisting of JL8, TCR27, JL7, TCR39, PEP-2, Ag36, JL9, TCNA, TcLo1.2, TS, TcD, TcE, FCaBP, Tc-28, Tc-40, FL-160, CEA, CRP, TcP2$\beta_N$-C29 and SA85-1.1.

DETAILED DESCRIPTION OF THE PRESENT INVENTION

Definitions

Figure 1:
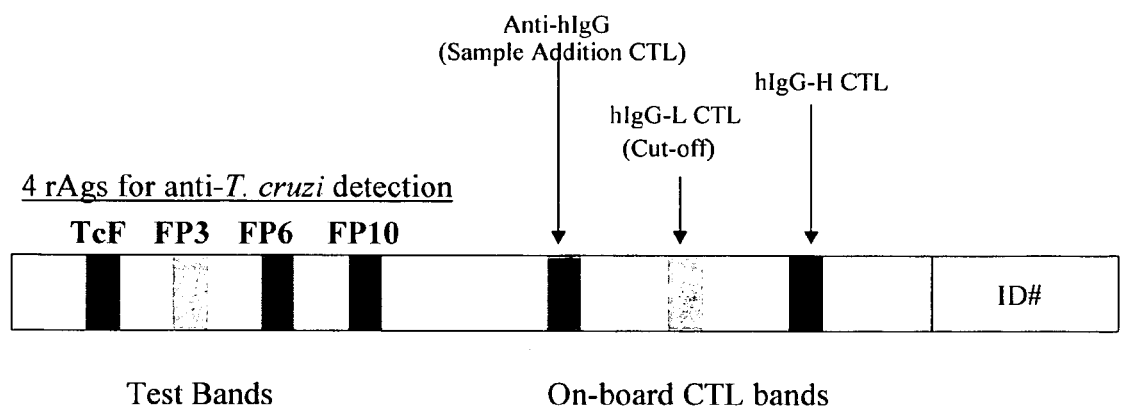
FIG. 1 shows an exemplary immunoblot strip. Four (4) recombinant antigens ("rags"), FP3, FP6, FP10 and TcF, are employed as Test Bands for the detection of antibodies to *T. cruzi*. Three (3) on-board control ("CTL") bands, goat anti-human IgG ("Anti-hIgG"), hIgG-low ("hIgG-L") and hIgG-high ("hIgG-H") can also be used. Goat anti-human IgG is used to verify sample addition, hIgG-L is used to set a cut-off for band intensity, and hIgG-H is used as reference for bands with higher intensity. The results anticipated using the strip can be described as follows. For a negative control, the three (3) on-board control bands are visible and no test bands are visible. For a positive control, in addition to the three (3) on-board control bands being visible, the four (4) test bands are also visible.

As used herein, the term "antibody" refers to an immunoglobulin molecule or immunologically active portion thereof, namely, an antigen-binding portion. Examples of immunologically active portions of immunoglobulin molecules include F(ab) and F(ab')$_2$ fragments which can be generated by treating an antibody with an enzyme, such as pepsin. Examples of antibodies that can be used in the present invention are polyclonal antibodies, monoclonal antibodies, chimeric antibodies, human antibodies, humanized antibodies, recombinant antibodies, single-chain Fvs ("scFv"), an affinity maturated antibody, single chain antibodies, single domain antibodies, Fab fragments, F(ab') fragments, disulfide-linked Fvs ("sdFv"), and anti-idiotypic ("anti-Id") antibodies and functionally active epitope-binding fragments of any of the above.

As used herein, the term "FP3" refers to a refers to a recombinant fusion polypeptide (antigen) derived from *T. cruzi* having the antigenic domain shown in Table 1 and the amino acid sequence shown in the sequence of SEQ ID NO: 1. Methods of making FP3 are described, e.g., in U.S. Patent Publication No. 2004/0132077 now U.S. Pat. No. 7,491,515 B2 issued Feb. 17, 2009, the contents of which are herein incorporated by reference. The term "FP3" as used herein also encompasses variants of this amino acid sequence that differ in conservative substitutions and/or modifications.

As used herein, the term "FP6" refers to a refers to a recombinant fusion polypeptide (antigen) derived from *T. cruzi* having the antigenic domain shown in Table 1 and the amino acid sequence shown in the sequence of SEQ ID NO: 2. Methods of making FP6 are described, e.g., in U.S. Patent Publication No. 2004/0132077 now U.S. Pat. No. 7,491,515 B2 issued Feb. 17, 2009, the contents of which are herein incorporated by reference. The term "FP6" as used herein also encompasses variants of this amino acid sequence that differ in conservative substitutions and/or modifications.

As used herein, the term "FP10" refers to a refers to a recombinant fusion polypeptide (antigen) derived from *T. cruzi* having the antigenic domain shown in Table 1 and the amino acid sequence shown in the sequence of SEQ ID NO: 3. Methods of making FP10 are described, e.g., in U.S. Patent Publication No. 2004/0132077 now U.S. Pat. No. 7,491,515 B2 issued Feb. 17, 2009, the contents of which are herein incorporated by reference. The term "FP10" as used herein also encompasses variants of this amino acid sequence that differ in conservative substitutions and/or modifications.

As used herein, the term "TcF" refers to a recombinant fusion polypeptide (antigen) derived from *T. cruzi* having the antigenic domain shown in Table 1 and the amino acid sequence shown in the sequence of SEQ ID NO: 4. Methods of making TcF are described in U.S. Pat. No. 6,419,933, the contents of which are herein incorporated by reference. The term "TcF" as used herein also encompasses variants of this amino acid sequence that differ in conservative substitutions and/or modifications.

TABLE 1

| | Antigenic Domain | Description* |
|---|---|---|
| FP10 | SAPA[a] | Shed acute phase antigen |
| | MAP[a] | Microtubule-associated protein |
| FP6 | TcR39[a] | Cytoskeletion/membrane protein |
| | FRA[b] | Flagellar repetitive protein |
| FP3 | TcR27[c] | protein |
| | FCaBP[d] | Flagellar |
| TcF | PEP-2[b] | GDKPSPFQA AA GDKPSPFGQA |
| | TcD[b] | AEPKS AEPKP AEPKS |
| | TcE[b] | KAATAPA KAAAAPA KAATAPA |
| | TcLo1.2[b] | SSMP S GTSEEGSRGGSSMPA |

*The underlining highlights segments of amino acid repeats.
[a]N-terminal, repeats, and C-terminal segments included.
[b]Comprised entirely of repeats (PEP-2 is SEQ ID NO: 5; TcD is SEQ ID NO: 6; TcE is SEQ ID NO: 7 and TcLo1 .2 is SEQ ID NO: 8).
[c]N-terminal and repeats included.
[d]Full-length, non-repetitive protein.

As used herein, the terms "subject" and "patient" are used interchangeably. As used herein, the terms "subject" and "subjects" refer to a mammal, including a human or an animal. Preferably, the subject is a human.

As used herein, the term "test sample" refers to a biological sample derived from serum, plasma, whole blood, saliva, cerebrospinal fluid, urine, or other bodily fluids or appropriate sample for testing of a subject. The test sample can be prepared using routine techniques known to those skilled in the art. The test sample also includes samples from a blood supply intended for transfusion.

As used herein, the term "variant(s)" as used in connection with a polypeptide (such as, but not limited to, the recombinant fusion polypeptides, FP3, FP6, FP10 and TcF) refers to a polypeptide that differs from an identified amino acid sequence by substitution, deletion or the addition of five amino acids or fewer. Such variants may generally be identified by modifying the polypeptide sequence and evaluating the antigenic properties of the modified polypeptide. Polypeptide variants exhibit at least about 70%, more preferably at least about 90% and most preferably at least about 95% identity (as described herein) to the identified polypeptides. As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. Generally, change within the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. Variants may also, or alternatively, contain other modifications, including the deletion or addition of amino acids that have minimal influence on the antigenic properties, secondary structure and/or hydropathic nature of the polypeptide.

Methods of Identifying *T. cruzi* in a Sample

The present invention relates to methods of identifying antibodies to *T. cruzi* in a test sample. The methods involve obtaining a test sample from a subject that is suspected of having been exposed to *T. cruzi* or of being infected with *T. cruzi*. Once the requisite test sample has been obtained, the test sample is contacted with the four recombinant polypeptides (or antigens), FP3, FP6, FP10 and TcF. Once the test sample is contacted with the four recombinant polypeptides, the presence or absence of antibodies to each of the polypeptides is then determined in the test sample and compared to (1) a predetermined cut-off value, or (2) the intensity of signal generated by one or more controls. In an alternative embodiment, the methods described herein can also be used for detecting *T. cruzi* infection in blood supplies. In still yet a further alternative embodiment, the methods described herein can be used to diagnose *T. cruzi* infection in a subject.

There are a variety of different assay formats that are well-known to those skilled in the art that can be employed using the four recombinant polypeptides FP3, FP6, FP10 and TcF herein to detect antibodies to *T. cruzi* in a test sample. For example, in one assay format, one or more of the recombinant polypeptides can be immobilized on a solid support to bind to and remove one or more antibodies from the test sample. The bound antibody or antibodies can then be detected using a detectable label that binds to the polypeptide/antibody complex and contains the detectable label. Alternatively, a competitive assay can be utilized, in which an antibody that binds to one or more of the recombinant polypeptides may be utilized, in which an antibody that binds to one or more of the polypeptides is labeled with a detectable label and allowed to bind to the immobilized recombinant polypeptide after incubation with the recombinant polypeptide in the test sample. The extent to which components of the test sample inhibit the binding of the labeled antibody to one or more recombinant polypeptides is indicative of the reactivity of the sample with one or more of the immobilized polypeptides.

In terms of the detectable label, any detectable label known in the art can be used. For example, the detectable label can be a radioactive label (such as, e.g., $^3$H, $^{125}$I, $^{35}$S, $^{14}$C, $^{32}$P, and $^{33}$P), an enzymatic label (such as, e.g., horseradish peroxidase, alkaline peroxidase, glucose 6-phosphate dehydrogenase, and the like), a chemiluminescent label (such as, e.g., acridinium esters, luminal, isoluminol, thioesters, sulfonamides, phenanthridinium esters, and the like), a fluorescence label (such as, e.g., fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, *Introduction to Immunocytochemistry*, 2$^{nd}$ ed., Springer Verlag, N.Y. (1997) and in Haugland, *Handbook of Fluorescent Probes and Research Chemicals* (1996), which is a combined handbook and catalogue published by Molecular Probes, Inc., Eugene, Oreg.

The solid support can be any material known to those of ordinary skill in the art to which the four (4) recombinant proteins can be attached. Examples of solid supports that can be used are a test well in a microtiter plate, nitrocellulose, nylon, a bead or a disc (which can be made out of glass, fiberglass, latex, plastic or a paper material), a gel (for example, a gel through which the polypeptides have been run and which is subsequently dried) or a strip, disc or sheet (which can be made out of nitrocellulose, nylon, plastic or paper). The preferred assay format for the methods of the present invention is an immunoblot assay in a flow-through or strip test format. In the flow-through or strip test format, the solid support is in the form of a strip, disc or sheet that is made out of nitrocellulose, nylon, plastic or paper. More preferably, the recombinant polypeptides described herein are immobilized on said strip, disc or sheet. Most preferably, the recombinant proteins are arranged as separate, parallel bands, spots or dots on the strip, disc or sheet (each of which may be referred to as a "test" band, spot or dot, collectively as "test" bands, spots or dots). The recombinant proteins can be immobilized on said strip, disc or sheet using routine techniques known in the art, such as automated techniques, such as by jetting the recombinant proteins on to said strip, disc or sheet (using a jetting instrument such as those available from Bio-Dot ((such as the AJQ3000 Air Jet Quanti or the RR 4200—Dip Tank), Irvine, Calif.) or manual techniques, such as by pipetting the recombinant proteins on to said strip, disc or sheet. If a sheet is used, once all of the recombinant proteins are immobilized onto the sheet, the sheet can be cut, using routine techniques known in the art into strips for use in an assay. The location of the recombinant proteins (and optionally, any controls) on the strip, disc or sheet is not critical. Additionally, the strip, disc or sheet can be further immobilized on a support layer using routine techniques known in the art, such as gluing, lamination, etc. The support layer can be made from plastic, cardboard, etc. For example, a nitrocellulose strip or disc can be laminated onto a pressure-sensitive plastic film. Further optionally, in addition to any discrete region employed for the location of an on-board control or test bands, spots or dots, the strip disc or sheet optionally comprises an identification region ("ID#" in FIG. 1) employed for labeling a sample such that it can be differentiated from other samples (e.g., name, number, alphanumeric reference, bar code, or other appropriate means).

The recombinant polypeptides (namely, FP3, FP6, FP10 and TcF) may be bound to or immobilized on to the solid support using any techniques known to those skilled in the art (for example, using a Western blot technique, the method for which is well known to those skilled in the art). In addition, and optionally, one or more controls can also be immobilized on to the solid support (such as for use in an immunoblot assay, namely, in a flow-through or strip test format). The terms "bound" or "immobilized" as used interchangeably herein, refer to both the noncovalent association, such as adsorption, and covalent attachment (which may be a direct linkage between the recombinant protein) and the functional groups on the solid support or may be a linkage that is effected by way of a cross-linking agent). Binding by adsorption to a strip, disc or sheet is preferred. In such instances, adsorption can be achieved by contacting solutions of each of the recombinant polypeptides, and optionally, any control in a suitable buffer, with the strip, disc or sheet for a suitable amount of time. The contact time will vary depending on the temperature, but is between about 1 hour and about 24 hours.

If necessary, covalent attachment of the recombinant polypeptides (and optionally, any controls) to a solid support can be achieved by first reacting the solid support with a bifunctional reagent that will react with both the support and a functional group, such as a hydroxyl or amino group, on the recombinant polypeptides. For example, the polypeptides may be bound to supports having an appropriate polymer coating using benzoquinone or by condensation of an aldehyde group on the support with an amine and an active hydrogen on the polypeptide.

Once the recombinant polypeptides (and optionally, any controls) are immobilized on the support, the remaining protein binding sites on the support are typically blocked. Any suitable blocking agent known to those of ordinary skill in the art can be used. For example, bovine serum albumin ("BSA"), phosphate buffered saline ("PBS") solutions of casein in PBS, Tween 20™ (Sigma Chemical Company, St. Louis, Mo.), as well as other blocking agents, can be employed. Optionally, for use of a support comprising a gel which is subsequently dried, blocking of the support may not be necessary. After blocking is completed, the support can optionally be washed, such as with PBS and allowed to dry (such as by air drying) for a suitable amount of time. The drying time will vary depending on the temperature, but is between about 30 minutes and about 24 hours.

The immobilized recombinant polypeptides (and optionally, one or more controls) are then allowed to incubate with the test sample. Prior to said incubation, the test sample may be diluted with a suitable diluent, such as PBS. During this incubation, if any antibodies are present in the test sample, these antibodies will bind to one or more of the recombinant polypeptides on the solid support. Generally, the incubation period is a period of time that is sufficient to permit the detection of the presence of *T. cruzi* antibodies within the test sample. Preferably, the incubation period is between about 15 minutes to about 6 hours. Most preferably, the incubation period is between about 1 hour and about 4 hours.

Unbound test sample may be removed by washing the solid support with an appropriate buffer, such as PBS or a Tris buffer (such as a Tris buffer containing 20 mM Tris, 0.15% Tween 20™ and 0.1% sodium azide). One or more detectable reagents can be added to the solid support. Appropriate detectable reagents are any compounds that binds to the immobilized polypeptide-antibody complex (and optionally any immobilized controls) and that can be detected by any of a variety of means that are known to those skilled in the art. Preferably, the detectable reagent contains a binding agent, such as, for example, Protein A, Protein G, an immunoglobulin, a lectin or a free antigen) conjugated to a detectable label. The conjugation of the binding agent to the detectable label can be achieved using standard methods known to those skilled in the art. Common binding agents may be purchased conjugated to a variety of detectable labels from a number of commercial sources, including, but not limited to Zymed Laboratories (San Francisco, Calif.) and Pierce (Rockford, Ill.).

One or more detection reagents are incubated with the immobilized polypeptide-antibody complex (and optionally, one or more controls) for an amount of time that is sufficient to detect the bound antibody or antibodies (and optionally, one or more controls). A suitable incubation time can generally be determined from the manufacturer's instructions or by assaying the level of binding that occurs over a period of time. Unbound detection reagent can then be removed and bound detection reagent is detected using the detectable label. The method used for detecting the detectable labels will depend on the nature of the detectable labels used in the assay. For example, for radioactive labels, scintillation counting or autoradiographic methods can be used. For chemiluminescent or fluorescent labels, spectroscopic methods can be used. Enzymatic labels can generally be detected by the addition of a substrate (usually for a specific period of time), followed by spectroscopic or other analysis of the reaction products.

To determine the presence or absence of *T. cruzi* antibodies in the test sample, the signal(s) detected from the detectable label(s) that remain bound to the solid support is compared to a pre-determined cut-off value. More specifically, this cut-off value can be the average mean signal obtained when the immobilized recombinant proteins are incubated with samples from a subject that is not infected with *T. cruzi*. In general, a test sample generating a signal that is three standard deviations above the mean is considered positive for *T. cruzi* antibodies and *T. cruzi* infection. Alternatively, if a light, darkness or color reading apparatus, such as a densitometer, that is capable of generating a numerical value is employed, the cut-off value can be determined using a Receive Operator Curve ("ROC"), using the method of Sackett et al., *Clinical Epidemiology: A Basic Science for Clinical Medicine*, p. 106-107 (Little Brown and Co., 1985). Briefly, the cut-off value may be determined from a plot of pairs of true positive rates (namely, sensitivity) and false positive rates (namely, 100% specificity) that correspond to each possible cut-off value for the diagnostic test result. The cut-off value on the plot that is the closest to the upper left-hand corner (namely, the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate. In general, a sample generating a signal that is higher than the cut-off value determined by this method is considered positive for *T. cruzi* infection. Preferably, the identification of a signal demonstrating the binding of antibodies to at least 2 of the 4 recombinant proteins FP3, FP6, FP10 and TcF indicates the presence of *T. cruzi* in said test sample.

As discussed previously herein, the preferred assay format is an immunoblot assay, namely, a flow-through or strip format, wherein four recombinant polypeptides FP3, FP6, FP10 and TcF are immobilized on a strip, disc or sheet, such as a nitrocellulose, nylon, plastic or paper strip, disc or sheet, as at least four separate test bands, spots or dots. The immobilization of each of these four recombinant polypeptides on a strip, disc or sheet can be obtained using the techniques described previously herein. Further recombinant polypeptides in addition to these four polypeptides (namely, FP3, FP6, FP10 and TcF) can also optionally be included in the strip, disc or sheet. Moreover, in addition to the four recombinant polypeptides, the strip, disc or sheet also contains immobilized thereon as separate test bands, spots or dots at least one control (each of which may be referred to as an "on-board control" band, spot or dot, collectively as "on-board control" bands, spots or dots). It is preferred that the strip, disc or sheet contain immobilized thereon two separate, discrete controls (namely, a first control and a second control), most preferably, the strip, disc or sheet can contain immobilized thereon three separate, discrete controls (namely, a first control, a second control and a third control). If more than one control is present, then the controls may be identical to one another or different from one another. Preferably, at least two of the controls are identical (such as, for example, the first control and the second control). If two of the controls are identical, it is preferred that the concentration of one of the controls (either the first control or the second control or if three controls are present, the first control or the third control or the second control or third control) immobilized on the strip, disc or sheet be higher (or greater) than the other control immobilized on the strip, disc or sheet. The control immobilized on the strip, disc or sheet in a higher concentration than the other control is referred to as the "high control". The control immobilized on the strip, disc or sheet in a lower concentration than the high control is referred to as the "low control". The ratio of the concentration of low control to high control present on the strip, disc or sheet can be from about 1:2 to about 1:10, preferably, about 1:5 to about 1:6. For example, the first control may be the low control and the second control may be the high control. Alternatively, the first control may be the high control and the second control may be the low control. By way of another example, the strip, disc or strip can contain 3 controls, namely, a low control and a high control as well a third control (which can be used, for example, to verify sample addition). The low control and high control can both be human IgG (wherein the ratio of low control to high control is from about 1:2 to about 1:10) and the third control can be a goat anti-human IgG.

In the flow-through format, one end of the strip, disc or sheet at which the recombinant polypeptides are bound can be immersed in a solution containing the test sample. Alternatively, the entire strip, disc or sheet can be placed in a reaction tray along with a diluent and then the test sample added to the reaction tray. The test sample and strip are allowed to incubate for a sufficient period of time using the same times and techniques described previously herein. Unbound test sample can be removed using the techniques described previously herein. In this format, antibodies within the test sample bind to the immobilized polypeptides (and the at least one control) as the test sample passes through the membrane. At least one detection reagent (such as a detection reagent described previously herein containing a detectable label) can be added. The at least one detection reagent binds to each of the polypeptides and polypeptide-antibody complexes formed as the solution containing the detection reagent flows through the strip. To determine the presence or absence of *T. cruzi* antibodies in the test sample, the detection of the bound detection reagents can be performed as described above using the a cut-off or by comparing the intensity of one or more signals generated by one or more controls as discussed in more detail below.

When a low control and high control as described above are used in the flow-through format, it is preferred that the presence or absence of the *T. cruzi* antibodies in the test sample be determined by identifying the presence of a signal from the detectable label at each of the test bands (or spots or dots) for the polypeptides. If a signal is identified at a test band for a polypeptide, then the intensity of this detected signal is compared with the intensity of the signal from the low control band (or spot or dot) and the high control band (or spot or dot), using a scale of 0 to 4+. The reading is 0 when no band is visible. The intensities of the low control band and high control band are defined as 1+ (for the low control) and 3+ (for the high control), respectively. A test band with an intensity comparable to that of the low control would be rated 1+. A band with intensity between that of the low control and the high control band would be rated 2+. A band with an intensity comparable to that of the high control would be rated 3+. A band intensity higher than that of the high control would be rated 4+. A faint band with intensity weaker than that of the low control would be rated ± (See Table 2). As shown in the exemplary algorithm depicted in FIG. 3, if the results of the immunoblot assay are that either (1) no bands are visible (other than the bands for the low control, high control and negative control); or (2) only a single band is visible (other than the bands for the low control, high control and negative control), then the test sample is deemed to be negative for *T. cruzi*. As also shown in the exemplary algorithm depicted in FIG. 3, if the results of the immunoblot assay are that two or more bands for the recombinant polypeptides demonstrate a signal, then the following analysis must be performed. Specifically, if all of the bands exhibit an intensity that is weaker than the low control, namely, all of the bands are rated ±, then the test sample is deemed to be indeterminate for *T. cruzi*. However, if at least one of the bands is rated 1+ or higher, then the test sample is considered to be positive for *T. cruzi* antibodies.

TABLE 2

| Intensity | Score |
|---|---|
| Absent | 0 |
| Faint or < on-board hIgG-L CTL | +/− |
| =on-board hIgG-L CTL | 1+ |
| Between on-board hIgG-L CTL and hIgG-H CTL | 2+ |
| =on-board hIgG-H CTL | 3+ |
| >on-board hIgG-H CTL | 4+ |

The assays described above may be performed using more than the four recombinant polypeptides described herein. Examples of other recombinant *T. cruzi* polypeptides that can be used, include, but are not limited to, JL8, TCR27, JL7, TCR39, PEP-2, Ag36, JL9, TCNA, TcLo1.2, TS, TcD, TcE, FCaBP, Tc-28, Tc-40, FL-160, CEA, CRP, TcP2$\beta_N$-C29 and SA85-1.1. The amino acid sequences and methods for making each of these recombinant polypeptides are well known to those skilled in the art. For example, the amino acid sequences for PEP-2, TcD and TcE are disclosed in U.S. Pat. No. 6,054,135. The polypeptides JL8, TCR27, TCR39, Ag36, JL9, TCNA and FCaBP are discussed in Frasch, A. C. C. et al., "Comparison of genes encoding *Trypanosoma cruzi* antigens." *Parasitol. Today* 7:148-151 (1991). The polypeptide Tc-28 is discussed in Abate, T. et al., "Cloning and partial characterization of a 28 kDa antigenic protein of *Trypanosoma cruzi*." *Biol. Res.*, 26:121-130 (1993). The nucleotide and deduced amino acid sequence of Tc-40 cDNA is described in Lesenechal, M. et al., "Cloning and characterisation of a gene encoding a novel antigen of *Trypanosoma cruzi*." *Mol. Biochem. Parasitol.*, 87:193-204 (1997). The polypeptides FL-160 and SA85-1.1 are discussed in Centron, M. S. et al. "Evaluation of recombinant trypomastigote surface antigens of *Trypanosoma cruzi* in screening sera from a population in rural Northeastern Brazil endemic for Chagas disease." *Acta Trop.*, 50:259-266 (1992). The polypeptide CEA is discussed in Jazin, E. E. et al. "*Trypanosoma cruzi* exoantigen is a member of a 160 kDa gene family." *Parasitol.*, 110:61-69 (1995). The amino acid sequence for CRP (identified as CRP-10) is described in Norris, K. A. et al., "Identification of the gene family encoding the 160-kilodalton *Trypanosoma cruzi* complement regulatory protein." *Infect Immun.* 65:349-357 (1997). The polypeptide JL7 is discussed in Umezawa, E S, et al., *J. Clinical Microbiology*, 37:1554-1560 (1999) and Cotrim, P C, et al., *J. Clinical Microbiology*, 28:519-524 (1990). The polypeptide TcLo1.2 is discussed in Houghton, R L, et al., *J. Infectious Diseases*, 179:1226-1234 (1999). The polypeptide TcP2$\beta_N$-C29 is described in Aguirre, S., et al., *J. Clin. Microbiology*, 44(10):3768-3774 (October 2006).

Additionally, the immunoassay can be revised to further include polypeptide antigens for the detection of other diseases, disorders or conditions, especially for the detection of other parasitic diseases. Along with the parasites that cause Chagas' disease (American trypanosomosis), the parasites which cause African sleeping sickness (African trypanosomosis) and leishmaniasis cause deadly human diseases that affect half a billion of the world's poorest people. Thus optionally, an immunoblot according to the invention further comprises polypeptides for the detection of other parasitic diseases such as African sleeping sickness and/or leishmaniasis.

By way of example, and not of limitation, examples of the present invention shall now be given.

Example 1

Immunoblot Assay Format

Immunostrip preparation. Solutions of human IgG-high concentration ("IgG-H"), human IgG-low concentration ("IgG-L"), goat anti-human IgG (the 3 on-board control bands), as well as the recombinant antigens ("rAgs") FP10, FP6, FP3, and TcF (the 4 test bands) were prepared. Specifically, each protein was dissolved in a pH 7, 20 mM sodium 3-(N-morpholinol-2-hydroxypropanesulfonate buffer. Using a microprocessor controlled XYZ3050 dispensing system from Bio-Dot (Irvine, Calif.) 1 micro-liter per cm of each protein was jetted on to nitrocellulose membrane sheets (0.45 micron, 5×30 cm; Whatman Schleicher & Schell, Keene, N.H.) in parallel lines in the relative positions depicted in FIG. 1. The concentrations of the jetting solutions were as follows: TcF at 75 microgram/ml; FPP3 at 0.4 microgram/ml; FP6 at 0.7 microgram/ml; FP10 at 6 microgram/ml; goat anti-human IgG at 25 microgram/ml; IgG-L at 2.5 microgram/ml and 15 microgram for IgG-H. After drying (37° C., 30 minutes), the membrane was blocked with 1% casein in phosphate buffered saline ("PBS"), washed several times in PBS, and again air-dried. As a final step, the membrane sheet was laminated with a pressure sensitive plastic film and cut into 4 mm wide strips. The loading of the proteins was adjusted so that the negative control specimen (FIG. 2, strip 1) did not show any test bands (other than the control bands— goat anti-human IgG, IgG-L and IgG-H) and the positive control specimen (FIG. 2, strip 2) showed 4 test bands, while in both cases the 3 control bands were reactive. A panel of reactive samples (FIG. 2, strips 3 to 6) showed 1 to 4 test bands, in addition to the 3 control bands.

Control specimens. The negative control was recalcified normal human plasma that tested negative in assays for the hepatitis B surface antigen ("HBsAg") and for antibodies to the core protein of hepatitis B virus ("HBcore"), hepatitis C virus ("HCV"), human immunodeficiency virus ("HIV") and human T-cell lymphotrophic virus ("HTLV"). The *T. cruzi* antibody positive control was from a pool of several plasma units drawn from blood donors diagnosed with Chagas' disease. The positive plasma was confirmed positive by several *T. cruzi* antibody tests, including ELISA-I (a lysate-based test commercially available in Latin America), ELISA-II (a 510(k)-cleared test based on recombinant antigens), and RIPA.

Test procedure. Positive and negative control specimens were included with each run. Previously frozen serum or plasma samples were microfuged (14,000 rpm, 5 minutes) in 1.5-ml Eppendorf tubes prior to testing to remove particulate matter; samples that had never been frozen were not centrifuged. 1 ml of diluent and an immunostrip were placed in each trough of an immunoblot reaction tray (Bio-Rad, Hercules, Calif.) and incubated for 5 min. During each incubation step the contents of the troughs were gently mixed on a rocker. A 20-μl sample was added to each trough containing a strip in diluent and incubated at ambient temperature for 2 hours, followed by aspiration and three washes with a Tris buffer (pH 8.0, 20 mM Tris, 0.15% Tween-20, and 0.1% sodium azide). One ml of an alkaline phosphatase-conjugated goat anti-hIgG solution was added to each trough. After a one hour incubation, each trough was aspirated and washed three times. Following this, 0.7 ml of a substrate solution of 5-bromo-4-chloro-3-indolylphosphate/nitro blue tetrazolium ("BCIP/NBT"; 1 tablet in 20 ml distilled water; Sigma-Aldrich, St. Louis, Mo.) was added to each well and incubated at ambient temperature for 10 minutes for color development. This was followed by aspiration and three washes with distilled water to stop color development. Subsequently, the strips were removed from the troughs and air-dried for visual reading. The total assay time was about 4 hours.

Interpretation of test results. *T. cruzi* antibody reactivity in a test specimen is determined by visual comparison of the intensities of the 4 test bands with the intensities of the two IgG control bands at the top of the strip, using a scale of 0 to 4+. The reading is 0 when no band is visible, and the intensities of the IgG-L and IgG-H control bands is defined as 1+ and 3+ respectively. With these landmarks in mind, a test band with intensity comparable to that of the human IgG-L control would be rated 1+; a band with intensity between that of the IgG-L control and that of the IgG-H control would be rated 2+; a band with intensity comparable to that of the IgG-H control would be rated 3+; and a band intensity higher than that of the IgG-H control would be rated 4+. Finally, a faint band with intensity weaker than that of the IgG-L control would be rated ±.

Other serologic assays. The Abbott PRISM® Chagas assay (Abbott Laboratories, Abbott Park, Ill.) was performed as described previously in Chang, C. D., et al., *Transfusion* 46:1737-1744 (2006). The RIPA was carried out as outlined earlier (See, Kirchoff, L. V., et al., *J. Infect. Dis.*, 155:561-564 (1987) and Kirchoff, L. V., et al., *Transfusion*, 46:298-304 (2006)), and all RIPA testing was done blindly.

Chagasic specimens. A total of 345 *T. cruzi* antibody positive human serum or plasma specimens were obtained from the American Red Cross, Antibody Systems (Hurst, Tex.), BioClinical Partners (Franklin, Mass.), Biocollections Worldwide, Inc. (Miami, Fla.), Boston Biomedica, Inc. (BBI, West Bridgewater, Mass.), Goldfinch Diagnostics Inc. (Iowa City, Iowa), Teragenix Corp. (Ft. Lauderdale, Fla.), and the Federal University of Bahia (Salvador, Bahia, Brazil). These specimens came from persons who acquired *T. cruzi* in most of the Central and South American countries, as well as Mexico and the United States (See, Table 3, below). All of them were positive in 2 or 3 conventional *T. cruzi* immunoassays (IHA, IFA, and ELISA) and also in the RIPA.

TABLE 3

| Country of Origin | # of Samples |
|---|---|
| Argentina | 40 |
| Bolivia | 53 |
| Brazil | 126 |
| Chile | 5 |
| Columbia | 1 |
| Ecuador | 1 |
| El Salvador | 12 |
| Honduras | 1 |
| Mexico | 17 |
| Nicaragua | 16 |
| Surinam | 1 |
| USA | 4 |
| Venezuela | 21 |
| Unknown | 44 |

Random donor population. A total of 500 specimens from randomly selected donors (sera (150) and EDTA plasma (350)), were obtained from Gulf Coast Regional Blood Center (Houston, Tex.). These unlinked specimens were collected from random donors and no specimens were eliminated from this group because of positive results in any of the six routine tests done on donated units. All specimens were tested within 10 days of collection in both the immunoblot assay and the Abbott PRISM® Chagas assay. All reactive samples with S/CO values of 0.90 or greater in the Abbott PRISM® Chagas assay were tested in ELISA-I, ELISA-II, and RIPA.

Potentially problematic specimens. A total of 271 archived sera or plasma specimens, serologically positive for other diseases or containing potentially interfering substances, were run in the immunoblot assay. This group included specimens from persons with cytomegalovirus ("CMV") (n=4), Epstein-Barr Virus ("EBV") (n=14), hepatitis A virus ("HAV") (n=10), helminths or intestinal protozoans (n=5), HIV (n=10), herpes simplex virus ("HSV") (n=15), leprosy (n=15), rubella (n=10), syphilis (n=10), toxoplasmosis (n=5), tuberculosis (n=3), yeast (n=10), varicella-zoster virus ("VZV") (n=10), hemolysis (n=20), hyper-IgG (n=10), hyper-IgM (n=10), hyperbilirubinemia (n=10), hypertriglyceridemia (n=15), influenza vaccinated (n=15), multiple myeloma (n=15), multiple sclerosis (n=5), rheumatoid factor (n=15), human anti-mouse antibodies (n=15), systemic lupus erythematosis (n=11), and leishmaniasis (n=9). They were purchased from various vendors including New York Biologicals (New York, N.Y.), ProMedDx (Norton, Mass.), SeraCare Life Sciences, Inc. (West Bridgewater, Mass.), and Hemacare Bioscience (Ft. Lauderdale, Fla.). These 271 samples were tested in the immunoblot assay of the present invention and the prototype Abbott PRISM® Chagas assay. All specimens that were repeatedly reactive in the latter were tested in the ELISA-I, ELISA-II, and then confirmed further with RIPA.

Figure 2:
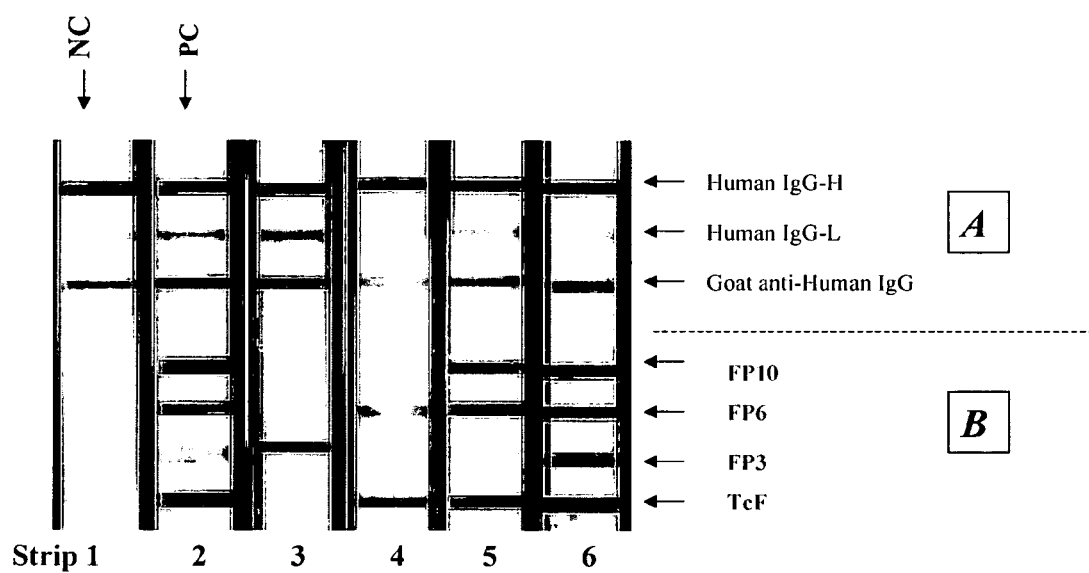
FIG. 2 shows the typical results obtained an exemplary immunoblot assay of the invention in terms of reactivity with test antigens FP3, FP6, FP10 or TcF or control antigens hIgG-H, hIgG-L or goat anti-human IgG. Strip 1 is a negative control ("NC"), showing three bands in the on-board control section (Box A); Strip 2 is a *T. cruzi* antibody positive control ("PC"), showing four test bands (Box B) in addition to the three on-board control bands (Box A); Strips 3-6 show samples containing one to four test bands (Box B) in addition to the on-board control bands (Box A).

Results. Results obtained with the immunoblot assay of the present invention are shown in FIG. 1, where the locations of the three on-board control bands and the four rAg (FP10, FP6, FP3 and TcF) test bands are clearly evident. All 345 *T. cruzi* antibody positive specimens showed two or more test bands in the immunoblot assay. A total of 277 of these specimens showed four test bands, 60 showed three bands, 8 showed two bands, and of note, none showed a single band or was entirely negative. Most test bands with the positive samples showed intensity equal or higher than the IgG-L control band (1+). Moreover, all 345 specimens were reactive in the Abbott PRISM® Chagas assay and in ELISA-II. In contrast, six of the 272 specimens in this group of 345 that were tested in ELISA-I were negative, although all six had above-baseline S/CO values, ranging from 0.60 to 0.89 (See, Table 4, below). These discordant samples were confirmed as weak positives on RIPA and showed two or three test bands on the immunoblot assay, with at least one band intensity of 1+ or higher. Due to the lower detection level of ELISA-I observed in testing the first 272 positive specimens, it was dropped from further sensitivity comparisons with other assays on newly acquired chagasic samples, although it was used to cross check repeatedly reactive samples from the Abbott PRISM® Chagas assay.

Figure 3:
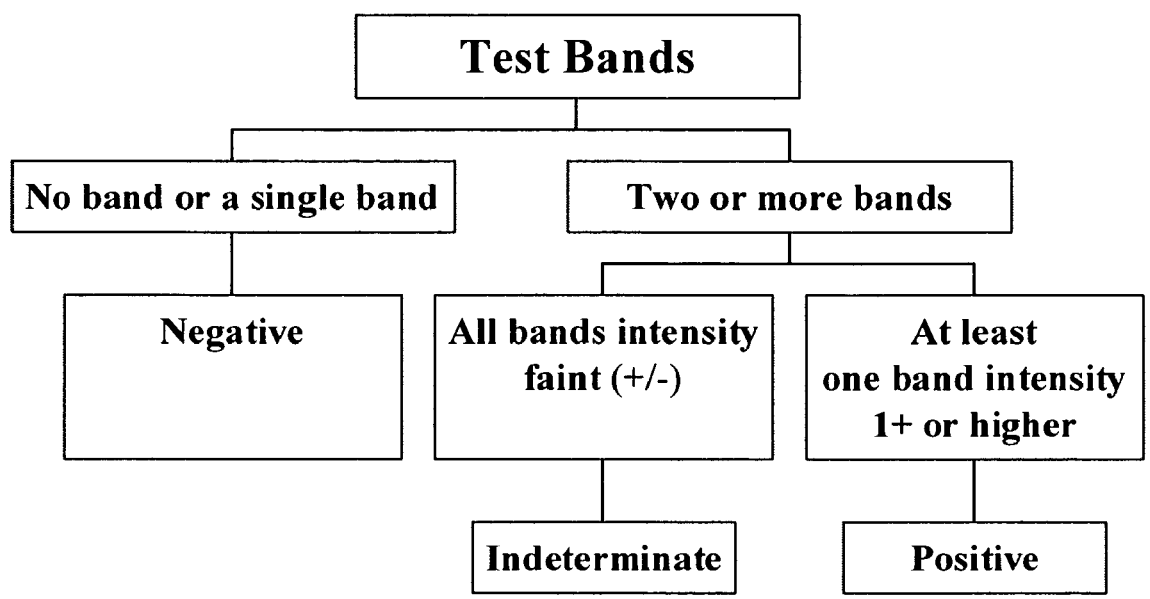
FIG. 3 is a schematic depiction of an exemplary algorithm for interpreting readings in the immunoblot assay of the present invention. The test bands are the test bands which are comprised of the recombinant antigens, FP10, FP6, FP3 and TcF. For each individual assay to be valid, the three on-board control bands also must be included on the immunoblot (e.g., must be present on the strip) and must be detected by the assay.

Based on the results obtained by testing these three groups of specimens, which total 1,116, the following scheme can be used for interpreting the patterns of test bands that appear on the immunostrips: a) no band or a single band—negative; b) two or more bands with at least one band having intensity of 1+ or higher—positive; and c) multiple faint bands (±)—indeterminate (See, FIG. 3).

When this scheme is applied to the patterns of test bands obtained with the 345 T. cruzi antibody positive specimens, all are deemed positive, thus giving a sensitivity of 100%

TABLE 4

| Sample ID | ABBOTT Chagas Assay S/CO | ELISA-I (Lysate) S/CO | ELISA-II (rAg) S/CO | RIPA | Immunoblot | |
|---|---|---|---|---|---|---|
| | | | | | Test bands present | Interpretation |
| Rag-40218 | 4.40 | 0.66 | 2.62 | +(weak) | Two | Positive |
| Rag-40224 | 3.86 | 0.77 | 3.56 | +(weak) | Three | Positive |
| RR04 | 1.52 | 0.83 | 3.02 | +(weak) | Three | Positive |
| RR52 | 2.07 | 0.83 | 3.56 | + | Three | Positive |
| RR115 | 1.50 | 0.60 | 3.53 | +(weak) | Two | Positive |
| RR334 | 2.37 | 0.89 | 3.35 | +(weak) | Two | Positive |

The 500 random donor specimens were tested in the immunoblot assay of the present invention and also in the prototype Abbott PRISM® Chagas assay. In the immunoassay of the present invention, one specimen gave a single 1+ test band and two others showed a faint (±) test band. None of these samples was reactive in the Abbott PRISM® Chagas assay nor in either of the two ELISAs; hence, these samples were not sent for RIPA. In view of the negative results obtained with these three specimens in the three comparison assays, the limited reactivity seen in the immunoblot assay of the present invention appears to be non-specific.

Of the 271 specimens with various disease states or potentially interfering substances tested in the immunoblot assay of the present invention, 265 showed no test bands, four gave a single 1+ band, and two showed three test bands. The four specimens with a single test band were non-reactive in the Abbott PRISM® Chagas assay. However, both specimens showing three test bands were also reactive in the Abbott PRISM® Chagas assay, ELISA-I, and ELISA-II, and were confirmed as positive in the RIPA (See Table 5, below). Additionally, as shown in Table 5 below, three specimens that gave S/CO values above 0.90 in the Abbott PRISM® Chagas assay were not confirmed by RIPA and showed no test bands in the immunoblot assay.

(345/345). With the 500 random donor specimens, 497 showed no test bands, two showed a single 1+ band, and 1 showed a faint band (±); thus all are negative and the resolved specificity is 100% (500/500). Finally, using this scheme, the immunoblot assay of the present invention showed a resolved specificity of 100% (269/269) in the 271 specimens with disease states or interfering substances.

During the development of the Abbott PRISM® Chagas assay and the immunoblot assay, approximately 42,000 unlinked sera and plasma specimens from U.S. random donors were tested and it was found that 21 that were repeatedly reactive or in the gray zone on the Abbott PRISM® Chagas assay Six specimens in the latter group were reactive in ELISA-I and ELISA-II, and were confirmed as positive by RIPA (See Table 6, below). Five of these six specimens showed three or four test bands in the immunoblot assay and thus were interpreted as positive. The sixth specimen in this group, #5060, could not be tested in the immunoblot assay because it was depleted before development of the latter was begun.

TABLE 5

| Sample ID | Abbott PRISM® Chagas Assay S/CO | ELISA-I (Lysate) S/CO | ELISA-II (rAg) S/CO | RIPA | Immunoblot | |
|---|---|---|---|---|---|---|
| | | | | | Test bands present | Interpretation |
| Protozoan[a], 2e03 | 9.55 | 3.02 | 2.82 | Positive | Three | Positive |
| Leprosy[b], 3b10 | 9.96 | 2.36 | 2.92 | Positive | Three | Positive |
| HAMA[c], #1 | 11.92 | 0.32 | 1.10 | Negative | None | Negative |
| HSV-1, #2 | 0.92 | 0.65 | 0.15 | Negative | None | Negative |
| HSV-2, #4 | 4.01 | 0.65 | 0.26 | Negative | None | Negative |

[a]Brazilian donor, tested positive for intestinal protozoan
[b]Brazilian donor
[c]Human anti-mouse antibodies ("HAMA")

TABLE 6

| Sample ID | Abbott PRISM® Chagas Assay S/CO | ELISA-I (Lysate) S/CO | ELISA-II (rAg) S/CO | RIPA | Immunoblot Test bands present | Interpretation |
|---|---|---|---|---|---|---|
| #437 | 10.9 | 3.58 | 2.31 | + | Four | Positive |
| #5060 | 6.78 | 2.64 | 7.27 | + | NT* | NA |
| #161 | 7.85 | 2.89 | 8.10 | + | Four | Positive |
| #S2712 | 2.90 | 1.46 | 5.00 | +(weak) | Three | Positive |
| #S108677 | 1.58 | 1.13 | 2.74 | + | Three | Positive |
| #P91 | 7.92 | 2.53 | 3.20 | + | Four | Positive |

*NT = not tested due to insufficient volume

The remaining fifteen Abbott PRISM® Chagas assay-reactive specimens, most of which had relatively low S/COs, were all negative by RIPA (See Table 7, below). All were negative in ELISA-I, but two were reactive and two were in the gray zone in ELISA-II. In the immunoblot assay, eight of these 15 specimens showed no test bands and the other seven showed a single band, including #1660 which showed a single FP3 band as Strip 3 in FIG. 2. Thus all fifteen were resolved as negative when the interpretation scheme described above was applied.

TABLE 7

| Sample ID | Abbott PRISM® Chagas Assay S/CO | ELISA-I (Lysate) S/CO | ELISA-II (rAg) S/CO | RIPA | Immunoblot Test bands present | Interpretation |
|---|---|---|---|---|---|---|
| #P1497 | 2.92 | 0.26 | 2.23 | Neg | None | Negative |
| #P1660 | 2.64 | 0.42 | 2.75 | Neg | Single FP3 (2+) band | Negative |
| #P1705 | 1.50 | 0.45 | 0.13 | Neg | None | Negative |
| #P1788 | 1.05 | 0.37 | 0.13 | Neg | Single TcF faint (+/−) band | Negative |
| #P2171 | 1.66 | 0.47 | 0.14 | Neg | None | Negative |
| #P3881 | 1.61 | 0.23 | 0.12 | Neg | Single TcF faint (+/−) band | Negative |
| #P6257 | 2.13 | 0.47 | 0.14 | Neg | None | Negative |
| #P6817 | 2.65 | 0.88 | 0.58 | Neg | Single FP10 faint (+/−) band | Negative |
| #P7087 | 1.00 | 0.29 | 0.14 | Neg | Single FP6 faint (+/−) band | Negative |
| #P7957 | 2.25 | 0.56 | 0.90 | Neg | None | Negative |
| #P8956 | 0.90 | 0.77 | 0.18 | Neg | Single TcF faint (+/−) band | Negative |
| #P9026 | 1.12 | 0.42 | 0.16 | Neg | None | Negative |
| #P9228 | 1.81 | 0.24 | 0.17 | Neg | None | Negative |
| #P9807 | 1.00 | 0.38 | 0.34 | Neg | Single FP6 band | Negative |
| #S108760 | 1.83 | 0.64 | 0.95 | Neg | None | Negative |

The immunoblot Chagas assay of the present invention provides 14 distinct antigenic domains, including repetitive as well as non-repetitive segments, in only four test bands (See Table 1). This arrangement holds the potential for markedly reducing the risk of false negative reactions, while at the same time allowing for the simple interpretation scheme presented in FIG. 3. This interpretation scheme was developed by analyzing the results obtained by running in the immunoblot assay of the present invention in the three groups of positive and negative specimens described above. The results clearly indicate that reactivity in two test bands is required for a positive interpretation. The adoption of an interpretation scheme in which two reactive test bands are required for confirmation of anti-*T. cruzi* antibodies is in line with the interpretation of the western blots used to confirm HIV (See, Maldarelli, F., "Diagnosis of human immunodeficiency virus infection", p. 1506-1527. In G. L. Mandell, J. E. Bennett, and R. Dolin (eds.), *Principles and Practice of Infectious Diseases*. John Wiley & Sons, New York) and Lyme borreliosis (See, Aguero-Rosenfeld, M. E., *Clin. Microbiol., Rev.*, 18:484-509 (2005)) and with the recombinant immunoblot assay for antibodies to HCV (See, Tobler, L. H., *Transfusion*, 40:917-923 (2000)), all three of which require more than one reactive test band for positive identification of a specific infection.

Moreover, with respect to the immunoblot assay of the present invention, as indicated, in the group of 345 specimens known to be positive for antibodies to *T. cruzi* the sensitivity of the assay was 100%. This result was particularly interesting, given the geographic diversity of the specimens (See Table 3 above) and the fact that there was no pre-selection for high titers. All specimens in this group were reactive in the Abbott PRISM® Chagas assay and the recombinant ELISA-II, but six of the 272 specimens tested in the lysate-based ELISA-I were negative. All six were weak positives in the RIPA, and these results suggest that a broad range of reactivity with *T. cruzi* antigens was present in the group of 345 positives and that the immunoblot assay is capable of detecting low-titer positives.

In the two groups of presumably *T. cruzi* antibody negative specimens, the specificity of the immunoblot assay of the present invention was 100% when the interpretative scheme described above and shown in FIG. 3 was used. The 500 random donor specimens from Texas, all of which were negative in the immunoblot assay, were also negative in the Abbott PRISM® Chagas assay and the two ELISAs and thus were not tested in the RIPA. In the 271 potentially-cross reacting specimens tested, two Brazilian specimens, from patients with leprosy and an intestinal protozoan infection, were positive in the immunoblot assay (three test bands) and were also clearly positive in the other assays, including RIPA, thus suggesting that they are true positives (See, Table 5, above). The three U.S. specimens were reactive in the Abbott PRISM® Chagas assay and one was reactive by ELISA-II; however, all were negative in ELISA-I and RIPA. Importantly, none of these specimens showed any test bands in the immunoblot assay of the present invention, thus suggesting that the latter is a useful tool for resolving specimens that are discordant in other assays. Overall, the resolved specificity of the immunoblot assay in this challenging group of specimens was 100% (269/269).

Study of a final group of specimens also demonstrates the usefulness of the immunoblot assay of the present invention as a confirmatory test. As explained above, in studies of approximately 42,000 unlinked U.S. random donors, 21 specimens were reactive in the Abbott PRISM® Chagas assay or the immunoblot assay. Six of the samples were globally positive, and the five for which there was sufficient volume remaining were clearly positive in the immunoblot assay, showing three or four test bands (See Table 6, above). With respect to the results obtained with the other 15 specimens in the Abbott PRISM® Chagas assay (See Table 7, above), all of these specimens had relatively low S/COs in the Abbott PRISM® Chagas assay and were somewhat reactive but ultimately negative in the ELISA-I. Four of 15 specimens were reactive in ELISA-II. Importantly, all 15 specimens were negative in the RIPA, and again it merits mention that all RIPA testing was done blindly. Finally, all 15 specimens were also negative in the immunoblot assay. As is evident in Table 7, about half of the specimens showed some reactivity, but none were positive when the interpretation scheme described above and shown in FIG. 3 was used. Taking into consideration that these 15 specimens are perhaps the most challenging in the total group of 42,000 tested, it was unexpected that they were all resolved by the immunoblot assay of the present invention in a manner that was 100% concordant with the results of the RIPA. In conclusion, these findings and those generated by testing the other groups of specimens studied in this example indicate that the immunoblot assay of the present invention can provide an accurate test for the serological confirmation of chronic *T. cruzi* infection.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

---

What is claimed is:

1. A method of identifying *Trypanosoma cruzi* antibodies in a test sample comprising the steps of:
   contacting a test sample with recombinant polypeptides FP3 (SEQ ID NO:1), FP6 (SEQ ID NO:2), FP10 (SEQ ID NO:3) and TcF (SEQ ID NO:4); and
   detecting binding of antibodies present in said test sample to at least two of said recombinant polypeptides, presence of said binding of said antibodies to at least two of said recombinant polypeptides indicating presence of *Trypanosoma cruzi* antibodies in said test sample.

2. The method of claim 1, wherein the test sample is selected from the group consisting of blood, serum, plasma, saliva, cerebrospinal fluid and urine.

3. The method of claim 1, further comprising the step of contacting the test sample with at least one additional recombinant polypeptide selected from the group consisting of JL8, TCR27, JL7, TCR39, PEP-2, Ag36, JL9, TCNA, TcLo1.2, TS, TcD, TcE, FCaBP, Tc-28, Tc-40, FL-160, CEA, CRP, TcP2$\beta_N$-C29 and SA85-1.1.

4. A method of diagnosing *Trypanosoma cruzi* infection in a subject comprising the steps of:

contacting a test sample obtained from a subject with a solid phase, wherein said solid phase has immobilized thereon recombinant polypeptides FP3 (SEQ ID NO: 1), FP6 (SEQ ID NO: 2), FP10 (SEQ ID NO: 3) and TcF (SEQ ID NO: 4) as separate test bands, and a first control and a second control, further wherein either the first control or the second control is immobilized on the solid phase in a concentration that is less than the other control so as to comprise a low control;

contacting the solid phase with at least one detection reagent;

detecting binding of antibodies present in the test sample by identifying presence of a signal at each test band;

comparing intensity of any signal identified at a test band for a recombinant polypeptide with intensity of the signal of the low control;

wherein identification of a signal of at least two test bands of the recombinant polypeptides indicates presence of *T. cruzi* antibody in said test sample and a *T. cruzi* infection in said subject, provided that at least one of the signals identified at a test band for a recombinant polypeptide has an intensity comparable or higher to that of the low control.

5. The method of claim 4, wherein the test sample is selected from the group consisting of blood, serum, plasma, saliva, cerebrospinal fluid and urine.

6. The method of claim 4, wherein said solid phase is selected from the group consisting of nitrocellulose, nylon, plastic and paper.

7. The method of claim 4, the solid phase having further immobilized thereon at least one additional recombinant polypeptide selected from the group consisting of JL8, TCR27, JL7, TCR39, PEP-2, Ag36, JL9, TCNA, TcLo1.2, TS, TcD, TcE, FCaBP, Tc-28, Tc-40, FL-160, CEA, CRP, TcP2$\beta_N$-C29 and SA85-1.1.

8. The method of claim 4, wherein said solid phase is a strip having said polypeptides immobilized thereon.

* * * * *